United States Patent [19]

Majercik et al.

[11] Patent Number: 5,108,427
[45] Date of Patent: Apr. 28, 1992

[54] ACTIVE PUPILLARY PROSTHESIS

[76] Inventors: Stephen M. Majercik, 3396 Brook Point La., Cuyahoga Falls, Ohio 44223; Daffyd I. W. Cook, 11235 73 Avenue, Edmonton, Canada, T6G O7C

[21] Appl. No.: 638,336
[22] Filed: Jan. 7, 1991
[51] Int. Cl.⁵ ............................................. A61F 2/14
[52] U.S. Cl. ...................................... 623/4; 446/389; 446/392
[58] Field of Search ................. 623/4, 5; 446/14, 389, 446/392; 351/162

[56] References Cited

U.S. PATENT DOCUMENTS

| | | | |
|---|---|---|---|
| 2,721,316 | 10/1955 | Shaw | 623/66 |
| 2,760,483 | 8/1956 | Tassicker | 623/4 |
| 3,480,971 | 12/1969 | Smith | 623/4 |
| 3,507,552 | 4/1970 | Scott | 351/162 |
| 4,272,910 | 6/1981 | Danz | 446/389 |
| 4,332,039 | 6/1982 | LaFaente | 446/389 |
| 4,436,376 | 3/1984 | Fergason | 350/334 |
| 4,551,149 | 11/1985 | Sciarra | 340/407 |
| 4,601,545 | 7/1986 | Kern | 350/332 |

FOREIGN PATENT DOCUMENTS 8601996  4/1986  World Int. Prop. O. ............. 623/5

Primary Examiner—Randy C. Shay
Attorney, Agent, or Firm—Renner, Kenner, Greive, Bobak, Taylor & Weber

[57] ABSTRACT

An ocular prothesis is provided in which a prosthesis housing has a bore therein for receiving elements to simulate the iris and pupil of an eye. A black disc is received within the bore and covered by an active disc having a central aperture therethrough exposing a portion of the black disc to represent maximum pupil constriction. The active disc has one or more rings concentric with the aperture, such rings being made from a photochromic material such that at various light intensities the rings change from translucent to opaque. Accordingly, at low light levels with the rings transparent, a greater portion of the black disc is apparent, giving the appearance of a dilated pupil. As light levels increase, the rings sequentially become opaque from the largest ring to the smallest, giving the appearance of pupil constriction.

9 Claims, 1 Drawing Sheet

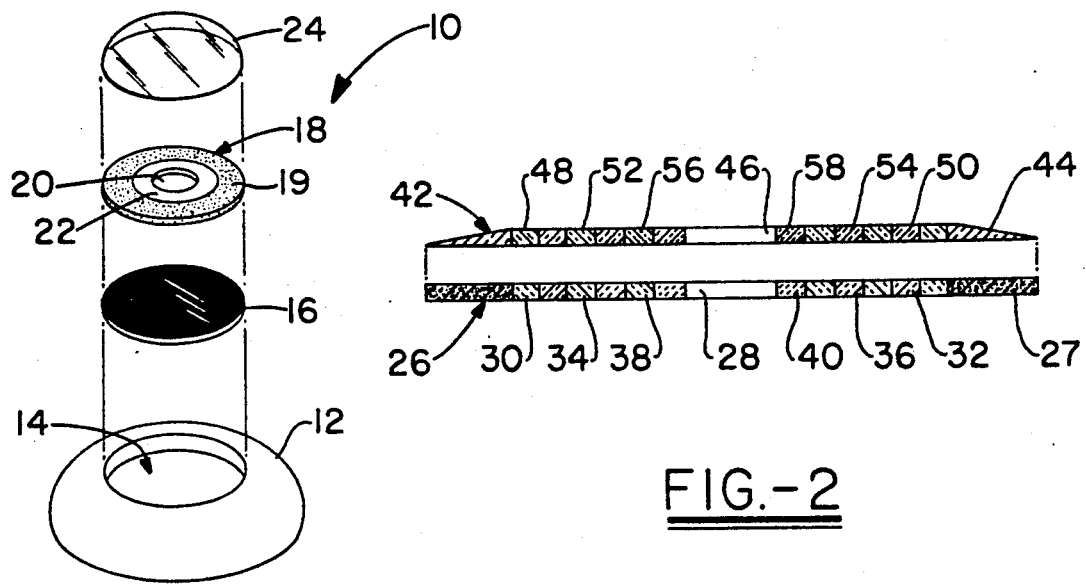
FIG.-2
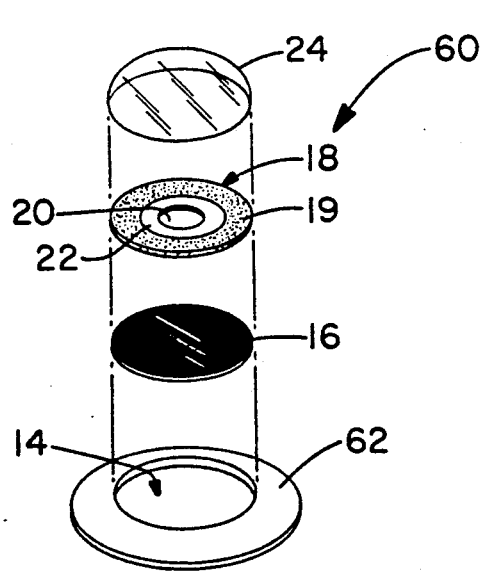
FIG.-1
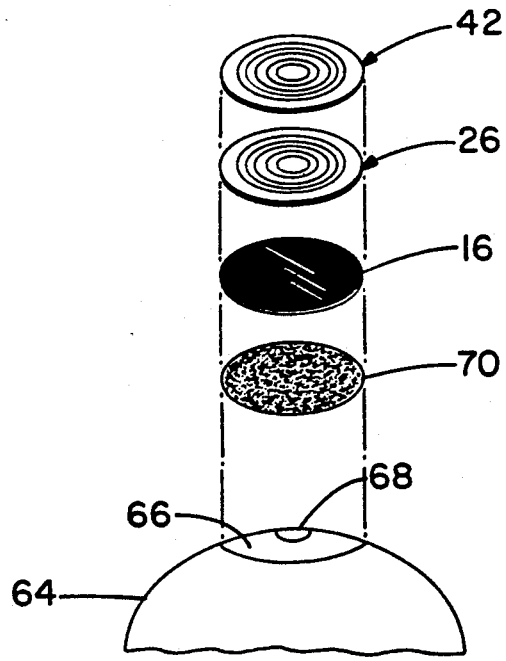
FIG.-3
FIG.-4

5,108,427

ACTIVE PUPILLARY PROSTHESIS

TECHNICAL FIELD

The invention herein resides in the art of ocular prostheses for enucleation replacement. Particularly, the invention relates to an optical or ocular prosthesis having a active pupil area which simulates dilation and contraction as a function of incident light. The invention further extends to a scleral shell and/or contact lens for correcting for the absence of an iris and/or globe.

BACKGROUND ART

The loss of an eye by accident or disease is not an uncommon occurrence. Further, some individuals are born without an iris, with a defective iris, or without a globe. Because such loss or defect impacts facial appearance, it is most desirable to either compensate for it, mask it, or provide some artificial means to replace it. One approach is to simply employ a patch to cover the eye and/or socket. However, a patch necessarily draws attention to the absence or inoperability of the eye. Accordingly, it does little to improve the physical appearance of the wearer, while often adding to the emotional stress incident to such loss or defect.

It has recently been known to replace a missing eye with a prosthesis often referred to as an "artificial" or "glass" eye. Prior to 1940, most ocular prostheses were constructed of ground glass. However, the shortage of such glass during World War II led to the creation of pyroplastic prostheses with thin glass overlays. These overlays had painted surfaces which resembled the human eye. Because the surface could only have one image, a person employing such a device would require a series of prostheses to simulate the pupillary size in exposure to varying degrees of light. In the absence of such multiple prostheses, the "artificial" nature of the prosthesis would become readily apparent when the pupil size of the prosthesis was different from that of the wearer's natural eye. Of course, as the wearer would pass through environments of various light intensities during the day, the pupil of the natural eye would necessarily dilate or contract, differing in appearance from that of the prostheses in the absence of the physical change in prostheses by the wearer.

In about 1960, a method for placing two or more images on a rotating cylinder within the prosthesis was developed. A magnetic wand was used to locate the desired image in the center of the pupullary field. While representing a significant improvement, the system was limited in that its size and weight was prohibitive, and the change in pupil size was necessarily mechanically attained.

U.S. Pat. No. 4,332,039 teaches a magnetic type of prosthesis of the type just discussed. U.S. Pat. No. 3,480,971 teaches a mechanical dilator which is responsive to muscle movement within the eye socket to achieve the desired control over pupil size. U.S. Pat. No. 4,272,910 teaches the utilization of a photosensor and liquid crystal plate to attain the appearance of dilation in an artificial eye, with such dilation being responsive to light stimulation.

U.S. Pat. No. 4,601,545, 2,760,483, 2,721,316, 4,551,149, 4,436,376, and British Patent 2,016,276 are viewed as being of general interest to the concept of ocular prosthesis of the type presented herein.

The prior art has recognized the need to simulate dilation and contraction of the pupil in an ocular prosthesis, but the devices presented to achieve such a feature have typically been complex, expensive, and given to problems incident to failure and maintenance. Additionally, the prior art structures have typically been heavy and cumbersome, often uncomfortable when received in the socket of the wearer. Typically, the prior art structures have either been mechanical magnetic, electronic, or electromechanical, all requiring periodic maintenance, repair of replacement.

The art is devoid of an active pupillary prosthesis which is absent moving parts or electronis control. It is further absent such a prostheis employing photochromic materials capable of simulating dilation and constriction without electrical or mechanical action, but by simple chemical reaction to incident light. Specifically, the art is devoid of such an active pupillary prosthesis in which the scleral shell to be received by an implant is integrally provided with such photochromic materials. The art is further devoid of an applique which may be adhered to an existing scleral shell to provide such an active pupillary feature. The art is further devoid of a contact lens employing photochronic materials for the appearance of an active pupillary response which may be received by a defective eye for cosmetic masking.

DISCLOSURE OF INVENTION

In light of the foregoing, it is a first aspect of the invention to provide an active pupillary prosthesis which requires neither mechanical, nor electrical, nor magnetic actuation or stimulation.

Another aspect of the invention is the provision of an active pupillary prosthesis which is rapidly responsive to changes in light intensities.

Still a further aspect of the invention is the provision of an active pupillary prosthesis which simulates pupillary dilation and contraction in degrees corresponding to light intensity.

Yet a further aspect of the invention is the provision of an active pupillary prosthesis which requires minimal care, maintenance, and replacement.

An additional aspect of the invention is the provision of active pupillary prostheis which is lightweight, introducing little strain on the supporting structure of the eye socket of the wearer.

An additional aspect of the invention is the provision of active pupillary prosthesis which is reliable and durable in use while being simple to implement with state of the art elements.

A further aspect of the invention is the provision of an active pupillary applique which may be adhered to a scleral shell of a previously existing ocular prosthesis.

Another aspect of the invention is the provision of a contact lens having an active pupillary feature which may be received by an eye for cosmetic correction of a defective iris or cornea.

The foregoing and other aspects of the invention which will become apparent as the detailed description proceeds are achieved by an active pupillary prosthesis, comprising: a housing for receipt by an eye socket; and a first disc received by said housing, said first disc comprising a photochromic material, rendered transparent or opaque as a function of light incident thereto.

Other aspects of the invention which will become apparent herein are attained by an ocular appliance, comprising: a housing; and a first disc received by said housing and comprising a plurality of concentric rings of photochromic material about a central opening, said photochromic material being transparent or opaque as a function of light intensity incident thereto.

DESCRIPTION OF DRAWINGS

For a complete understanding of the objects, techniques and structure of the invention reference should be made to the following detailed description and accompanying drawings wherein:

FIG. 1 is an assembly diagram of an ocular prosthesis made according to a first embodiment of the invention;

FIG. 2 is a cross sectional view of a photochromic disc and filter disc employed in a second embodiment of the invention;

FIG. 3 is an assembly diagram of a contact lens having an active pupillary feature according to the invention; and FIG. 4 is an assembly diagram of an active pupillary applique for adherence to a scleral shell.

BEST MODE FOR CARRYING OUT THE INVENTION

Referring now to the drawings and more particularly FIG. 1, it can be seen that an active pupillary prosthesis according to the invention is designated generally by the numeral 10. As shown, an ocular prosthesis or scleral shell housing 12, of plastic or other suitable material, is provided with a first side adapted for engagement with an implant within the eye socket of the wearer, to be moved by the muscles within the socket, and a cylindrical bore or recess 14 on the opposite side thereof. It will be appreciated that the bore 14 is of partial depth into the housing 12. Received within the bore 14, at the bottom thereof, is a backing disc 16, preferably of plastic or the like, and most preferably black in color. As will become apparent later herein, the backing 16 is employed to simulate the pupil in the prostheis 10.

An active cover disc 18 is received over the backing disc 16 within the bore 14. The active disc 18 serves to simulate the iris of the prosthesis 10 and is preferably formed of suitable plastic such as polycarbonate. The disc 18 includes an annular ring 19 which is color impregnated to match the natural iris color of the wearer, such color permeating the ring 19. A hole or aperture 20 is centrally positioned within the disc 18, allowing a portion of the backing disc 16 to be apparent therethrough. The portion of the disc 16 viewed through the aperture 20 would typically present the pupil size in is contracted state. The hole or aperture 20 may be formed as an actual void, or it may be simply a stable clear window of polycarbonate or the like.

As shown, a ring 22 is provided about the aperture 20 and is concentric therewith. The ring 22 constitutes an area of the disc 18 which is doped with a photochromic material such as that manufactured by PPG Chemical, Inc. under the trademark PHOTO-SOL. As is well known to those skilled in the art, photochromic materials of this nature are typically opaque when impinged by light exceeding a threshold intensity, while being transparent or translucent in the absence of light of such intensity. Typically, it is the ultraviolet (uv) component of the light which typically effects the transmissibility change of the photochromic material. It will be appreciated that photochromic materials responsive to infrared (IR) light or of any frequency along the light spectrum could be employed in keeping with the concept of the invention. When opaque, the photochromic material of the ring 22 is selected to match the color of the ring 19.

A clear plastic dome 24 is provided over the active disc 18 to simulate the corneal curvature of a natural eye. It should thus be appreciated that the structure of a first embodiment of the invention is attained by the placement of the black backing disc 16, active disc 18, and dome 24 into the bore 14 of the ocular prosthesis or scleral shell housing 12.

The assembly of the prosthesis 10 is typically received by an implant in the eye socket of the wearer and in some instances is adapted for movement by the ocular muscles remaining in the socket. When so placed, the prosthesis will give the appearance of a natural eye because the pupil thereof is active to the extent that it changes in size as a function of the ambient light level. When in areas of low light intensity, the ring 22 is substantially transparent, exposing the area of the black disk 16 equal in diameter to the outside diameter of the ring 22. This represents a dilated pupil or large pupil size which is customary of individuals in low light level areas. If the light intensity changes, the light incident to the ring 22 of photochromic material, exceeding a characteristic threshold of such material, causes the ring 22 to become opaque, taking on the natural color of the polycarbonate disc 18, such that the backing disc 16 is only apparent through the aperture 20. Accordingly, the pupil of the prosthesis 10 appears to be constricted, as is customary in areas of high light intensity. It is well known that the change in effective pupil size is attained automatically by the response of the photochromic material of the ring 22 to the incident light, requiring no activation by the wearer.

While the structure of FIG. 1 is a remarkable improvement over the prior art devices discussed earlier, it still affords only two effective pupil sizes. It has been found that by replacing the active disc 18 with a segmented active disc and filter arrangement, a plurality of pupil sizes can be devised and tailored to correlate with different light intensity. As shown in FIG. 2, an active disc 26 may be used to replace the disc 18. It will be appreciated that the disc 26 has an outer annular ring 27 which is also preferably of polycarbonate material, entirely colored with impregnated pigment to simulate the iris of the wearer. A fixed aperture of hole 28 is centrally positioned therethrough, the same corresponding substantially to the aperture 20 of the disc 18. A plurality of concentric rings 30–40 are formed of photochromic material such as PHOTO-SOL and are positioned as a portion of the disc 26 sharing a common center with the center of the aperture 28. Each of the concentric rings 30–40 reacts to ultraviolet light to change from substantially clear or transparent at low light levels to substantially opaque at higher light levels. The photochromic material of the rings 30–40 is selected to have a color, when opaque, that matches that of the annular ring 27. Of course, a characteristic threshold of light intensity controls the change over from substantially clear to substantially opaque.

Also provided as a part of this embodiment of the invention is a filter disc 42 which is substantially of the same diameter as the disc 26. The disc 42 comprises a clear polycarbonate outer ring 44 and central aperture 46 having substantially the same diameter as the aperture 28 and in alignment therewith. A plurality of clear concentric rings 48–58 of light filtering material are respectively aligned and congruent with the concentric rings 30–40. The strongest filter of the array is the inner most ring 58, closest to the aperture 46, with the rings progressively decreasing the filter strength to the outer most ring 48 which provides the least filtering of ultraviolet light. Accordingly, as light intensity progressively increases, the filter rings 48-58 progressively pass more light to their respectively associated rings 30-40 to effectively "constrict" the pupil in stages with increasing light.

With each of the filter rings 48-58 being uniquely associated with and congruent with a photochromic ring 30-40, it will be appreciated that at low light levels of filters 48-58 will block sufficient light that all of the rings 30-40 are transparent, exposing the black disk 16 to the greatest degree, equivalent to a dilated pupil. As light increases, the filter ring 46 will first pass sufficient light to the photochromic ring 30 to activate that ring to become opaque, closing the effective aperture by restricting the circular area of appearance of the disc 16. As the light intensity increases, the filter ring 50 will pass light sufficient to activate the photochromic ring 32, rendering it opaque, causing the iris to grow and the pupil to effectively constrict. The process continues as light intensity grows, with sequential rings of the filter assembly passing sufficient light that the associated photochromic rings are sequentially rendered opaque to further constrict the pupil aperture as the natural eye of the wearer. Of course, when the ring 40 is rendered opaque, the pupil size appears to be that of the congruent apertures 28, 46.

It will be readily appreciated by those skilled in the art that one could eliminate the filter disc 42 by making the concentric rings 30-40 of photochromic material of different sensitivities. In other words, the concentric rings 30-40 may be comprised of photochromic material having different characteristic thresholds at which the material changes from translucent to opaque. In such an embodiment, the outer most ring 30 would be made of photochromic material activated by the lowest level of light intensity to become opaque. Successive photochromic rings would have progressively higher thresholds such that the inner most photochromic ring 40 would be activated by the highest level of light intensity to become opaque. The same effective pupillary constriction and dilation as discussed above would be achieved from such a structure. At low levels of light, all of the rings 30-40 would be rendered transparent to simulate maximum pupil exposure. At the highest light levels, all of the rings 30-40 would be opaque to simulate maximum iris and minimum pupil size. The rings 30-40 would sequentially switch from transparent to opaque with sequentially increasing light intensity levels.

It will be readily appreciated that the physical size and structure of the prosthesis 10 will be dictated by the dimensions necessary to obtain a "natural appearance." Typically, the rings 30-40 and 48-58 would have inside diameters of from 2.5 mm to 9.0 mm. The apertures 20, 28, 46 would, accordingly, have diameter on the order of 2.5 mm. Additionally, the outside diameter of the discs 18, 26, 42 would typically be on the order of 11.5 mm, having an inside diameter on the order of 9.0 millimeters. Such discs would also have a typical thickness on the order of 1 millimeter. Accordingly, it will be appreciated that the structure of the prosthesis 10 will be lightweight, given to comfortable use by the wearer over long periods of time.

The concept of the invention is also applicable to implementation as an opaque contact lens for use in cosmetically correcting the appearance of eyes which are absent an iris or have a defective iris or cornea. A contact lens, adapted for receipt by the eye, may be devised from the pupillary prosthesis 10 of FIG. 1, by simply replacing the ocular prosthesis housing 12 with a disc. Such contact lens 60 is shown in FIG. 3, with the disc 62 replacing the housing 12. the remaining elements of the assembly 60 remain substantially the same as those of the assembly 10. The disc 62 may be substantially rigid, in which case it will have a curvature accommodating the surface of the eye as shown. It is also contemplated that the disc 62 may be of a "soft" flexible nature to adapt to the eye curvature. Both structures are well known in the art of contact lenses. It will be appreciated that the soft contact lens would obviate the need for the lens 24, with the disc 62 simply comprising a flexible flat disc receiving the backing disc 16 and active cover disc 18, themselves of a flexible nature.

It will further be appreciated that the active disc 26 and filter disc 42 of FIG. 2 may be employed with the disc 62 for increasing pupillary activity as discussed above.

The invention may also be used to retrofit existing scleral shells to include an active pupillary feature. As shown in FIG. 4, an existing scleral shell 64 has an iris 66 and pupil 68 painted thereon. An applique consisting of the backing disc 16, active disc 26, and filter disc 42 may be bonded to the scleral shell 64 by means of an appropriate adhesive 70. The applique 16, 26, 42 is preferably placed to cover the painted iris 66 and pupil 68. Of course, the more basic disc 18 of FIG. 1 may be used instead of the discs 26, 42.

Those skilled in the art will readily appreciate that the concept of the invention may be extended to applications other than medical cosmetic appliances. By way of example only, devices such as those presented above may be used in dolls or the like to simulate natural pupillary activity.

Thus it can be seen that the objects of the invention have been satisfied by the structure presented above. While in accordance with the patent statutes only the best mode and preferred embodiments of the invention have been presented and described in detail, it is to be understood that the invention is not limited thereto or thereby. Accordingly, for an appreciation of the true scope and breadth of the invention reference should be made to the following claims.

What is claimed is:

1. An active pupillary prosthesis, comprising:
a housing for receipt by an eye socket; and
a first disc received by said housing, said first disc having an aperture passing centrally therethrough and comprising a plurality of photochromic concentric rings encircling said aperture and rendered transparent or opaque as a function of light incident thereto, said photochromic concentric rings having different characteristic light sensitivities progressively from an inner ring to an outer ring.

2. The active pupillary prosthesis as recited in claim 1, further comprising a second disc interposed between said housing and said first disc, said second disc being substantially black in color and exposed by said aperture of said first disc and said rings in their transparent state.

3. The active pupillary prosthesis as recited in claim 1, wherein a photochromic concentric ring having a greatest diameter is activated to become opaque at a first light intensity, and a photochromic concentric ring having a smaller diameter is activated to become opaque at a second light intensity, said first light intensity being less than said second light intensity.

4. An active pupillary prosthesis, comprising:
a housing for receipt by an eye socket;
a first disc having an aperture passing centrally therethrough and received by said housing, said first disc comprising a plurality of photochromic concentric rings encircling said aperture and rendered transparent or opaque as a function of light incident thereto; and
a second disc adjacent said first disc, said second disc having a plurality of concentric light filter rings.

5. The active pupillary prosthesis as recited in claim 4, wherein respective ones of said filter rings are congruent with respective ones of said photochromic rings.

6. The active pupillary prosthesis as recited in claim 5, wherein a filter ring having a greatest diameter is a weaker filter than a filter ring having a smallest diameter.

7. An ocular appliance for simulating pupillary activity, comprising:
a housing;
a first disc received by said housing and comprising a plurality of concentric rings of photochromic material about a central opening, said photochromic material being transparent or opaque as a function of light intensity incident thereto; and
a second disc covering said first disc and comprising a plurality of concentric rings of light filtering material, respective rings of said filtering material being congruent with respective rings of said photochromic material.

8. The ocular appliance according to claim 7, further comprising a third disc, substantially black in color, positioned behind said first disc for exposure to simulate a pupil through said central opening and by actuation of said photochromic rings.

9. The ocular appliance according to claim 8, further comprising a lens over said first disc.

* * * * *